(12) United States Patent
Caritg

(10) Patent No.: US 6,398,550 B1
(45) Date of Patent: Jun. 4, 2002

(54) MOUTHPIECE FOR DENTAL IMPRESSIONS

(75) Inventor: André Caritg, Andorra la Vella (AD)

(73) Assignee: Difusio Dental Kera, Andorra la Vella (AD)

( * ) Notice: Subject to any disclaimer, the term of this patent is extended or adjusted under 35 U.S.C. 154(b) by 0 days.

(21) Appl. No.: 09/712,053

(22) Filed: Nov. 14, 2000

(30) Foreign Application Priority Data

Nov. 17, 1999 (DE) ..................................... 299 20 226 U
Jun. 15, 2000 (DE) ..................................... 200 10 403 U

(51) Int. Cl.⁷ ................................................. A61C 9/00
(52) U.S. Cl. ....................................................... 433/37
(58) Field of Search ............................. 433/34, 35, 36, 433/37, 38, 39, 40, 41, 42, 43, 44, 45, 46, 47

(56) References Cited

U.S. PATENT DOCUMENTS 5,890,894 A   4/1999   Mio et al. ..................... 433/37

FOREIGN PATENT DOCUMENTS

DE   1766510   3/1977
EP   0237389   9/1987

Primary Examiner—Cary E. O'Connor
(74) Attorney, Agent, or Firm—Harrison & Egbert

(57) ABSTRACT

The invention involves an impression tray for dental prosthetics. In order to perform the hardening of the impression material without having to have a worker manually hold the impression tray for the duration of the hardening, it is proposed to construct the impression tray so that it can be held by the patient's biting down. In this process it is proposed to equip the bottom of the impression material with a thickness that is enlarging from the ends, in order to obtain during biting only forces normal to the surfaces of the bottom. Instead of equipping the entire bottom in this self-reinforcing manner, it also possible to provide only a separately inserted casting channel with this special shape, which is also constructed in a special embodiment in such a manner that it can used in the impression trays known thus far.

10 Claims, 10 Drawing Sheets

MOUTHPIECE FOR DENTAL IMPRESSIONS

BACKGROUND OF THE INVENTION

1. Field of the Invention

The invention involves an impression tray for dental prosthetics, having a U-shaped running groove that has a bottom and two side walls.

2. Description of Related Art

Impression trays of this type are generally known in prophylactodontia. With them, impressions are taken of a jaw with teeth or its partial sections, for the subsequent manufacture of crowns, bridges, and other dental prostheses.

The impression trays correspond by their U-shaped contour essentially with the progression of the jaw whose impression should be taken.

Into the U-shaped running groove, a self-hardening impression paste is filled, and then an impression is made with it.

Using the impression, a positive model is then made later that functions for the dental technician's modeling of the dental prosthesis.

The self-hardening impression paste involves especially special silicone masses, which not only represent a considerable cost factor for the impression technology, but also, in their later disposal, can be a strain on the environment, for example, because as plastics they poorly decay in landfills.

An essential problem of the customary impression pastes, however, lies in the fact that for self-hardening, some time is spent in which the impression tray usually must be held in position by an assistant in order to obtain a precise impression. If during the hardening period, the impression tray is wobbled, this can lead to an imprecise impression.

The purpose of the invention presented here is thus to further develop an impression tray as described above in such a way that a secure handling can be achieved in which wobbling that is possibly caused by the assistant can be prevented.

BRIEF SUMMARY OF THE INVENTION

This purpose is achieved according to the invention in that the bottom has a thickness that is enlarging away from the ends of the legs.

Because of this special form of the bottom, the holding of the impression tray can be achieved during hardening in that the patient, on whose jaw the impression is taken, bites on the impression tray. In an impression tray with a bottom that has a constant thickness, as has been used thus far, there is the danger that the impression tray is first pressed on one end against the teeth to be molded and in this way can tilt which then leads to an imprecise impression. This is prevented by an impression tray according to the invention with a bottom that becomes thicker starting from the ends of the legs.

The invention is based on the knowledge that the lower jaw-bone (submaxilla) is moved around the mandibular joint in close approximation on a circular path. By the bottom with the thickness that is increasing from the ends of the legs, this movement is taken into account to such an extent since the bottom—in the side view—is constructed in a circular segment shape. It is thus impinged during biting both from the upper and from the lower jaw only by forces normal to its surface. A tilting, as described above for the impression tray known thus far, can thus no longer occur.

A patient can thus achieve the necessary compression pressure himself by biting on the impression tray, without having to have an assistant hold the impression tray when the material hardens. The assistant can thus be active in other work.

In an especially advantageous embodiment, the reinforcement of the bottom is constructed at an angle of less than 5°. This angle is felt to be especially pleasant by a patient, so that when he bites on the impression tray, he can apply the necessary press-on pressure over a longer time without tension.

In another preferred embodiment form, the upper side of the bottom has a progression that rises at the ends of the leg of the U-shape.

This embodiment form is based on the knowledge that the masticatory surfaces of the teeth do not lie in a plane, but instead define a curve from the rear to the front, the so-called Spee's curve. By the construction of the bottom according to this Spee's curve, the application of normal forces on the impression tray can be further supported during biting.

Also, the upper side of the bottom can have a lateral slope to the inside of the U-shape. In this way, it is observed that the masticatory surfaces of left and right buccal teeth lying opposite each other on the jaw do not lie on a straight line, but on a curve, the so-called Wilson's curve.

In an additional preferred embodiment form, the side walls of the U-shaped running groove are extended beyond the bottom and thus form a U-shaped counter-bite groove.

In this counter-bite groove, an impression paste can also be filled, so that an impression can be made simultaneously of the upper jaw (supermaxilla) and lower jaw (submaxilla). For the later modeling, it is namely advantageous to also have the counter-bite available each time.

Until now, it has been proposed in this regard to make separate impressions of the other jaw. For this purpose, the corresponding impression paste is filled into a separate impression tray, which means additional work and expense. With the shape of an impression tray proposed here now, the upper jaw and lower jaw can be molded simultaneously and the patient must be subjected to the unpleasant procedure of the impression only once. Aside from this fact, this also accelerates the work progression and takes up less time for the assistant who is occupied in making the impression.

It has also been found to be advantageous that in the bottom between the two grooves, holes going through are present. This not only leads to a secure connection between the impressions on the upper side and lower side of the impression tray, the impression paste can also hold better on the impression tray during a single impression, and thus there are no adhesives necessary or even retentions that cause a holding of the impression paste in the impression tray via a form closure. Retentions of this type are, however, difficult to clean later because of the undercuts, etc.

Instead of equipping the entire bottom of the impression tray with a thickness that is increasing away from the ends of the leg, it is also within the frame of the invention to provide the bottom of the impression tray with a bulge that runs along the U-shaped groove, which has a thickness that is increasing away from the ends of the leg. Also, with a bulge of this type, the effects can be achieved as described above.

In a preferred embodiment form of this bulge, it is constructed as a removable casting channel mold with a U-shaped progression, for the attachment of which a receptacle groove is worked into the bottom of the impression tray. In this process, it is preferable also to mold onto the impression tray, in the area of the base of the U-shaped groove, a handle that is provided with a hole that communicates with the groove, in which the casting channel mold can be inserted using a projection piece. This casting channel mold is essentially Y-shaped in this case.

In the process, the hole provided in the handle should advantageously have a cross-section that tapers conically to the groove. This conical tapering can also be done in steps.

With the impression tray, which is provided with a matching casting channel mold, there are not only the advantages as described above, that a patient applies only normal forces onto the impression tray in his mouth when he is biting, but there is also the possibility via the removable casting channel mold, for performing a multi-stage impression process: in this process, a preliminary impression can be made with the impression tray with an inserted casting channel mold, whereby the preliminary impression material is relatively coarse. After hardening of the preliminary impression material, the impression tray is taken out of the patient's mouth again and the casting channel mold is removed. It is to be assumed that the patient already has bitten on the casting channel mold, so that by removing the casting channel mold, connection holes are made at these biting positions between the casting channel on the one hand and the hollow space formed by the tooth, etc. On the other hand, connection holes of this type are still to be made, for example, with a scalpel or a similar tool.

After the impression tray is then inserted again into the patient's mouth, a low-viscous impression material can be introduced through the casting channel, which copies the areas to be molded in a more exact manner than the coarse preliminary impression material used at first.

In order to bring the low-viscous impression material into the casting channel, it is injected molded via the hole constructed in the handle as aforementioned. Thus, so that syringes can be connected for this purpose with the widest range of projection diameters, the hole provided for this construction is conically tapering. A syringe is pushed into the tapering hole as far as possible, whereby it then is affixed at the position that is the lowest possible for it.

The casting channel mold, which can also be used because of its cross-section that is tapering towards its ends in order to convert an impression tray according to the state of the art that has existed thus far into an impression tray with a bottom area or biting area that becomes thicker away from the ends of the impression tray, has in particular an essentially Y-shaped contour. Whereas in the process the ends, arranged in pairs as described, have a tapering cross-section as described, an additional stopper-shaped thickened area is provided on the singular cross-section. With it, the hole in the handle of the impression tray can be closed.

Furthermore, on the singular end of the Y-shaped casting channel mold, a handle loop can also be constructed. This makes it easier to pull the casting channel mold out of the casting channel in the hardened preliminary impression material. Moreover, it should also be pointed out that the casting channel mold is provided on its paired sections if necessary with tapering side struts. In this way, if necessary, a more exact guidance of low-viscous casting material can be achieved at points which lie far away from the actual main channel.

On the other hand, with side struts of this type, a fixation of the casting channel mold can also be achieved in the U-shaped groove of a traditional impression tray, before the casting channel mold is held there by casting material filled in the impression tray.

The respective conical construction of the casting channel not only has the advantage that the casting channel mold is easier to remove, but also, that low-viscous casting material injected into the casting channel is distributed uniformly.

BRIEF DESCRIPTION OF THE SEVERAL VIEWS OF THE DRAWINGS

Additional advantages and characteristics of the invention result from the following description of the embodiment examples.

DETAILED DESCRIPTION OF THE INVENTION

Figure 1:
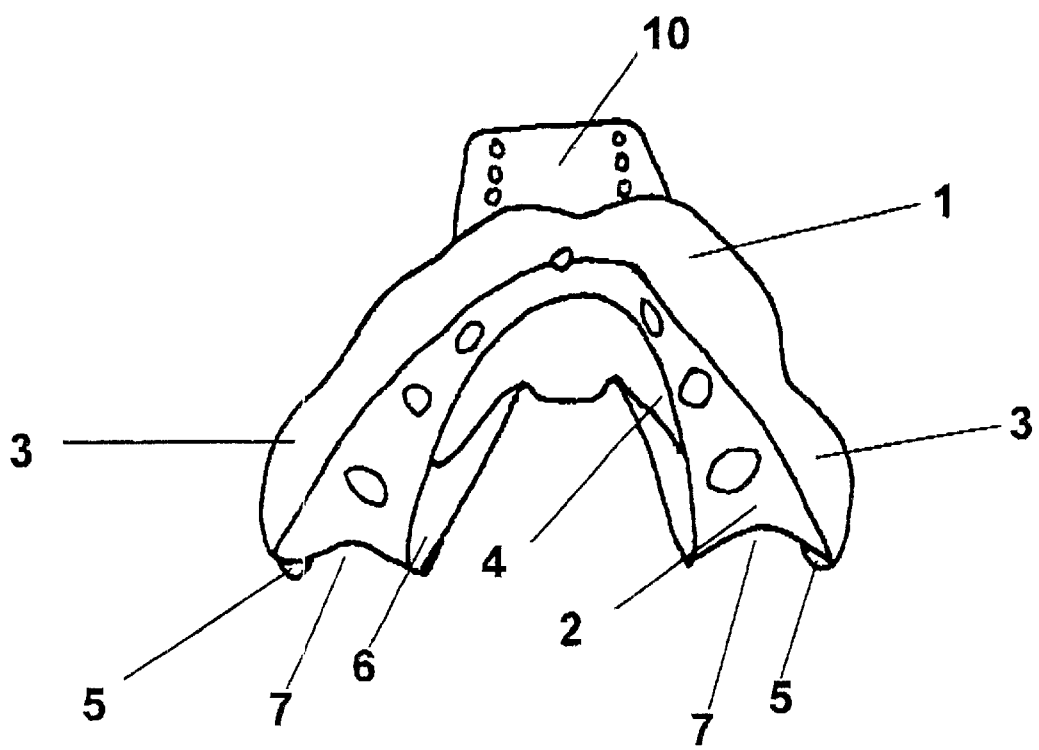
FIG. 1 an angled perspective view of the impression tray from above.

In FIG. 1, there is shown a view of an impression tray for dental prosthetics. This tray has a U-shaped running groove 1, which is formed by a bottom 2 and two side walls 3, 4.

The inner wall 4 forms, in the process, an arch that is closed to the top, which follows the palate in the patient's mouth.

Figure 2:
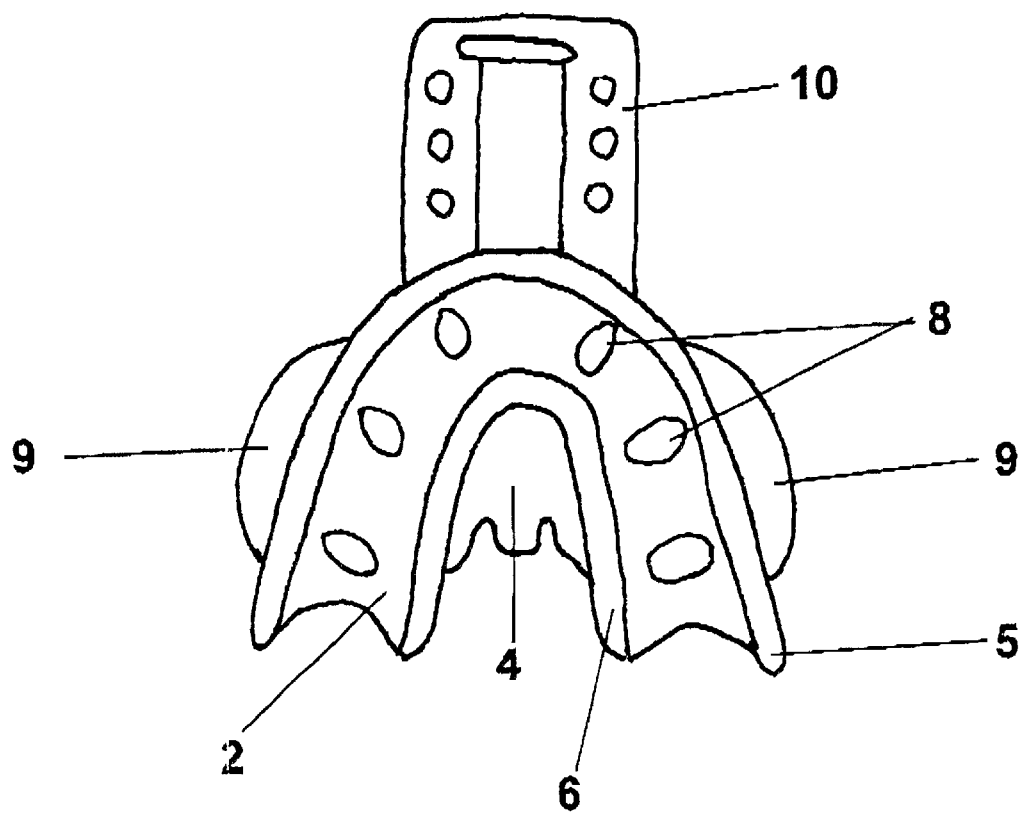
FIG. 2 a bottom view of an impression tray.

It is recognized that the side walls 3, 4 are extended beyond the bottom 2, whereby they form with these extended sections 5, 6 and the underside of the bottom 2, a counter-bite groove 7, which is also U-shaped. The U-shape is shown especially in FIG. 2, in which a corresponding impression tray is depicted in the view from below.

In this representation, the Figure clearly shows the penetrating holes 8 in the bottom 2. Their function will be explained further later.

An impression tray as depicted is customarily filled with a silicone and then put over the patient's jaw in order make an impression of the tooth locations that are present. So that during hardening a precise impression is obtained, the impression tray must be affixed. This is customarily done by a dental assistant firmly holding the impression tray. However, this has the disadvantage that the assistant is occupied during this time and cannot do other work.

Figure 3:
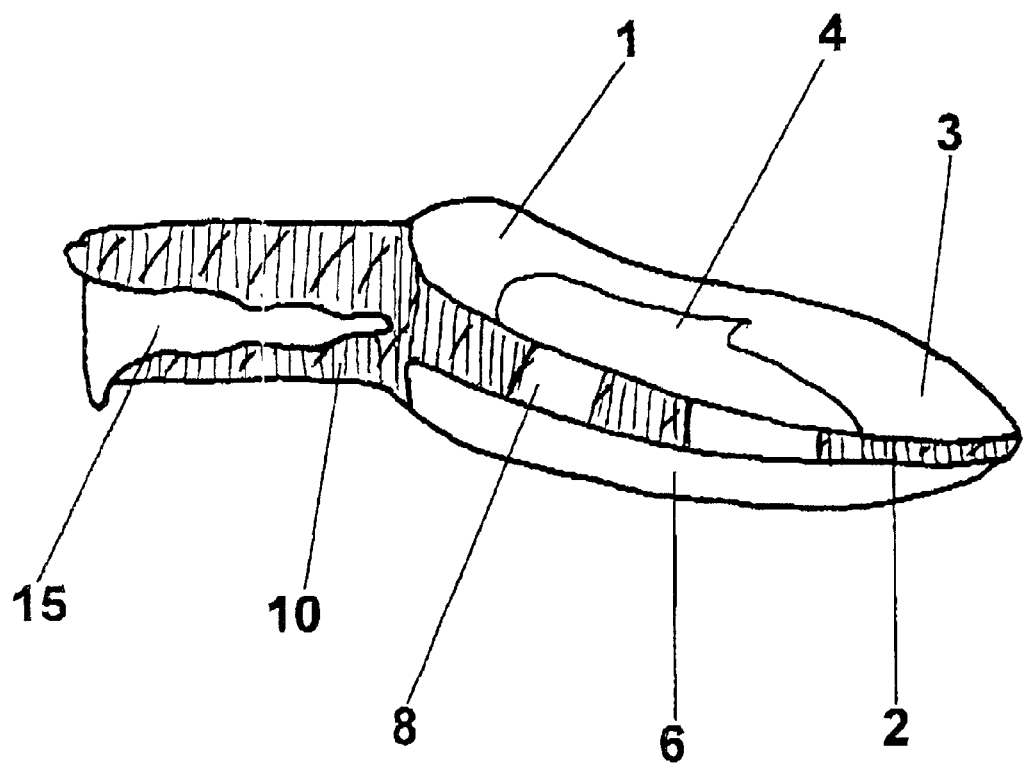
FIG. 3 a partial sectional side view of an impression tray.

With the impression tray described here, this can be avoided, since the bottom 2 has a thickness that is enlarging from the ends of the U-shaped groove 1, as is recognized in FIG. 3, in which an impression tray is shown with a section in the side view, which essentially follows the groove 1.

It is shown clearly in this drawing that the bottom 2 is considerably thinner on its one end—here lying to the right—than on its opposing end—here lying to the left. The increase of the thickness is constant and corresponds to an angle of inclination of approx. 5°.

By this increasing thickness, it can be achieved that a patient can hold the impression tray by biting. Since the lower jaw is moved approximately on a circular path around the mandibular joint, it is achieved by the bottom 2 that is increasing in thickness, that both on the upper as well as on the lower side of the bottom, the teeth act in the normal direction to the surface of the bottom, so that the bottom is not tipped during biting or the like, which would lead to a wobbling of the impression tray and thus to an inexact impression.

Furthermore, it is shown in FIG. 3, that the bottom 2 has a curved progression and thus rises especially on the ends of the U-shaped groove 1 opposite a hypothetical plane. This special progression takes into account the so-called Spee's curve, i.e. the curve on which the masticatory surfaces in a set of teeth lie.

As already mentioned, hardening silicone is put into the groove 1, before the impression tray is set on the set of teeth of a patient. The patient then bites down, such that he achieves a uniform distribution of forces in the impression tray because of the thickened bottom 2, so that no tilting of the impression tray occurs. During impression, excess casting material is forced both to the side on the side walls 3 and 4 up as well as through the penetrating holes 8 mentioned above. During the hardening, the impression material gets caught in these penetrating holes 8 so that during the subsequent removal of the impression tray from the set of teeth, it is ensured the hardening impression material is anchored in the impression tray.

So that the impression tray is easy to remove, impression straps 9 are provided on the outer side of the side walls 3. A dental assistant can grab these straps in order to take the impression tray off of the patient's jaw. Since these impression straps are directly adjacent to the U-shaped groove filled with casting material, a tilting is also prevented in the process, as could occur if an attempt is made to shape the impression tray via the handle 10 present on the impression tray.

Figure 6:
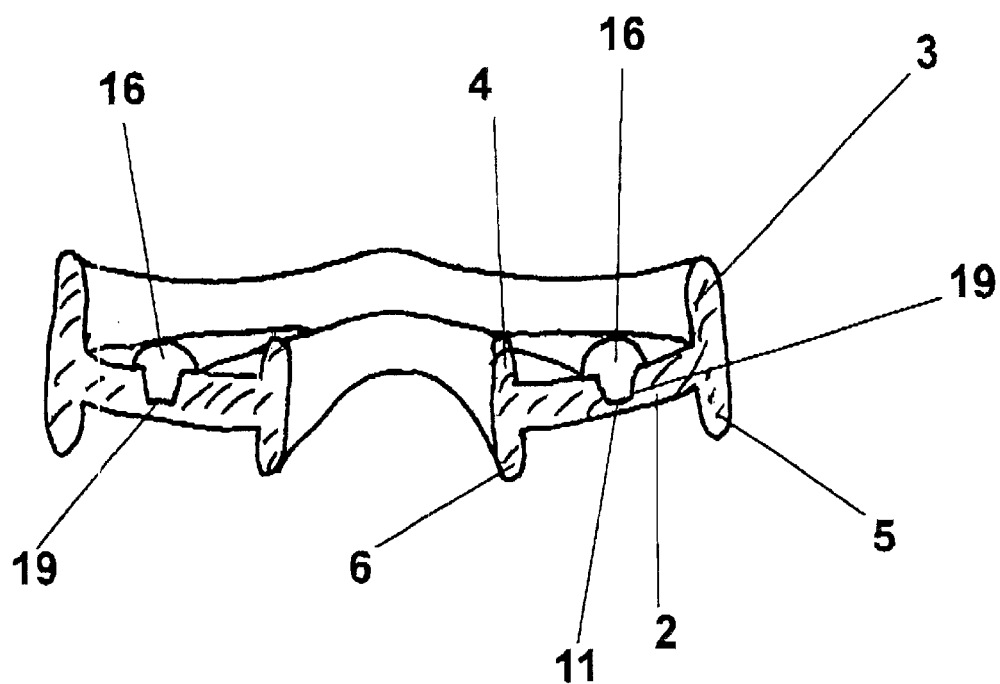
FIG. 6 a sectional view of an impression tray according to line VI—VI in FIG. 4 with an inserted casting channel mold.
Figure 7:
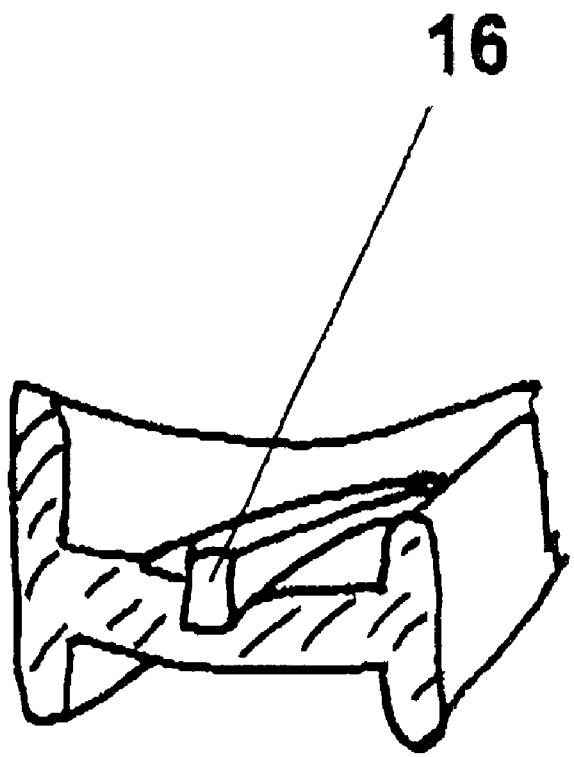
FIG. 7 a perspective view according to FIG. 6 with an alternative embodiment form of a casting channel mold.
Figure 8:
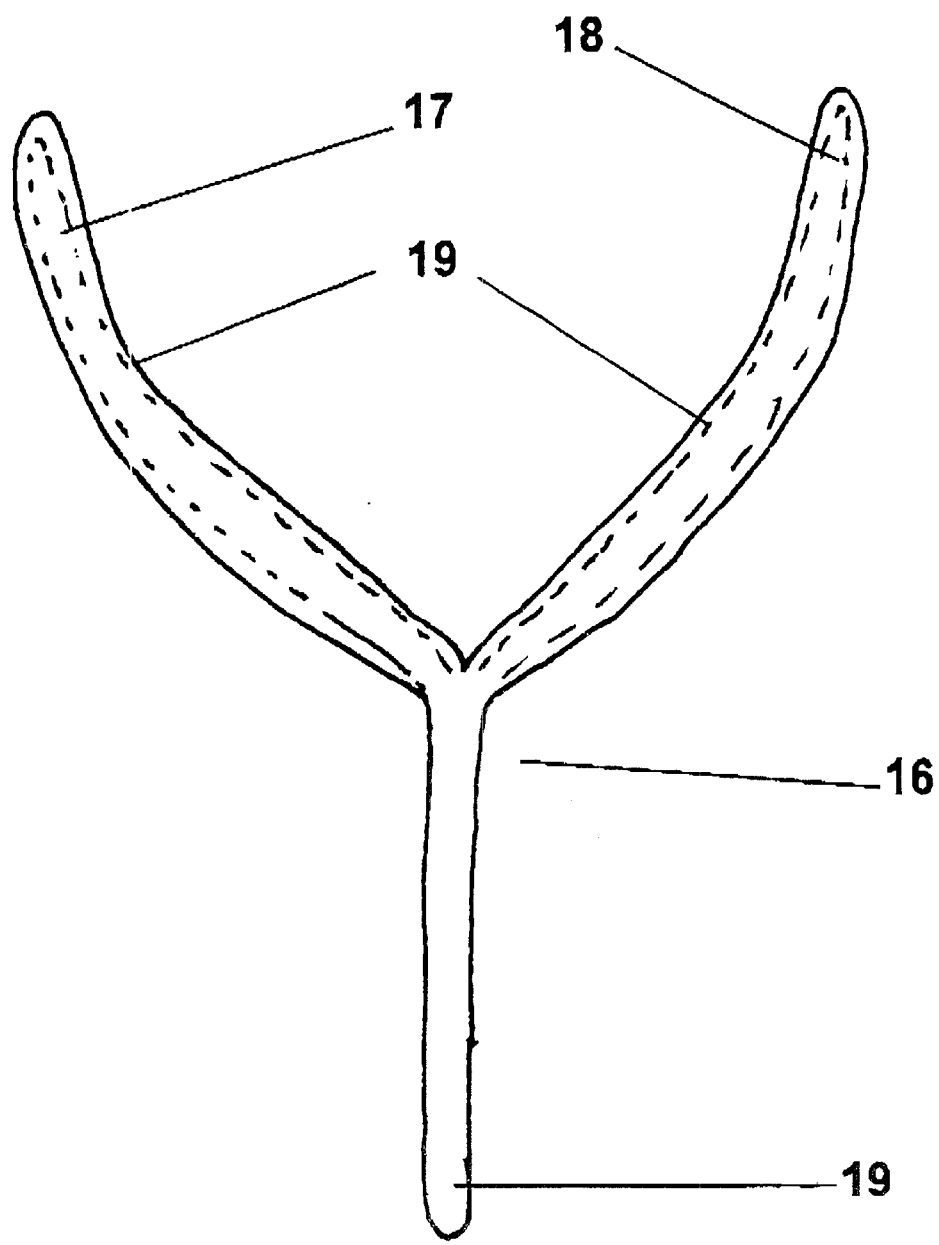
FIG. 8 a sectional view of a casting channel mold.
Figure 9:
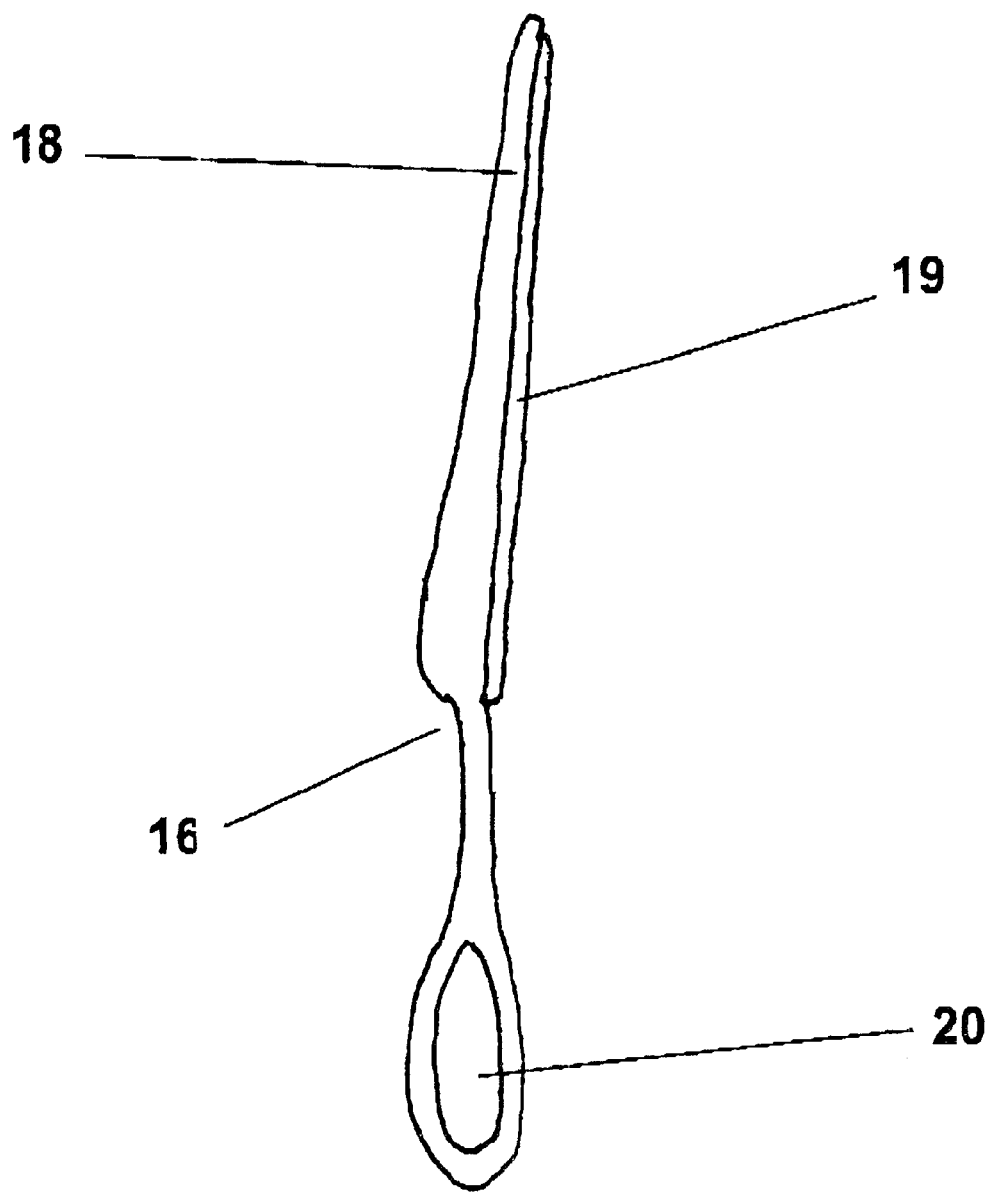
FIG. 9 a side view of a casting channel mold.
Figure 10:
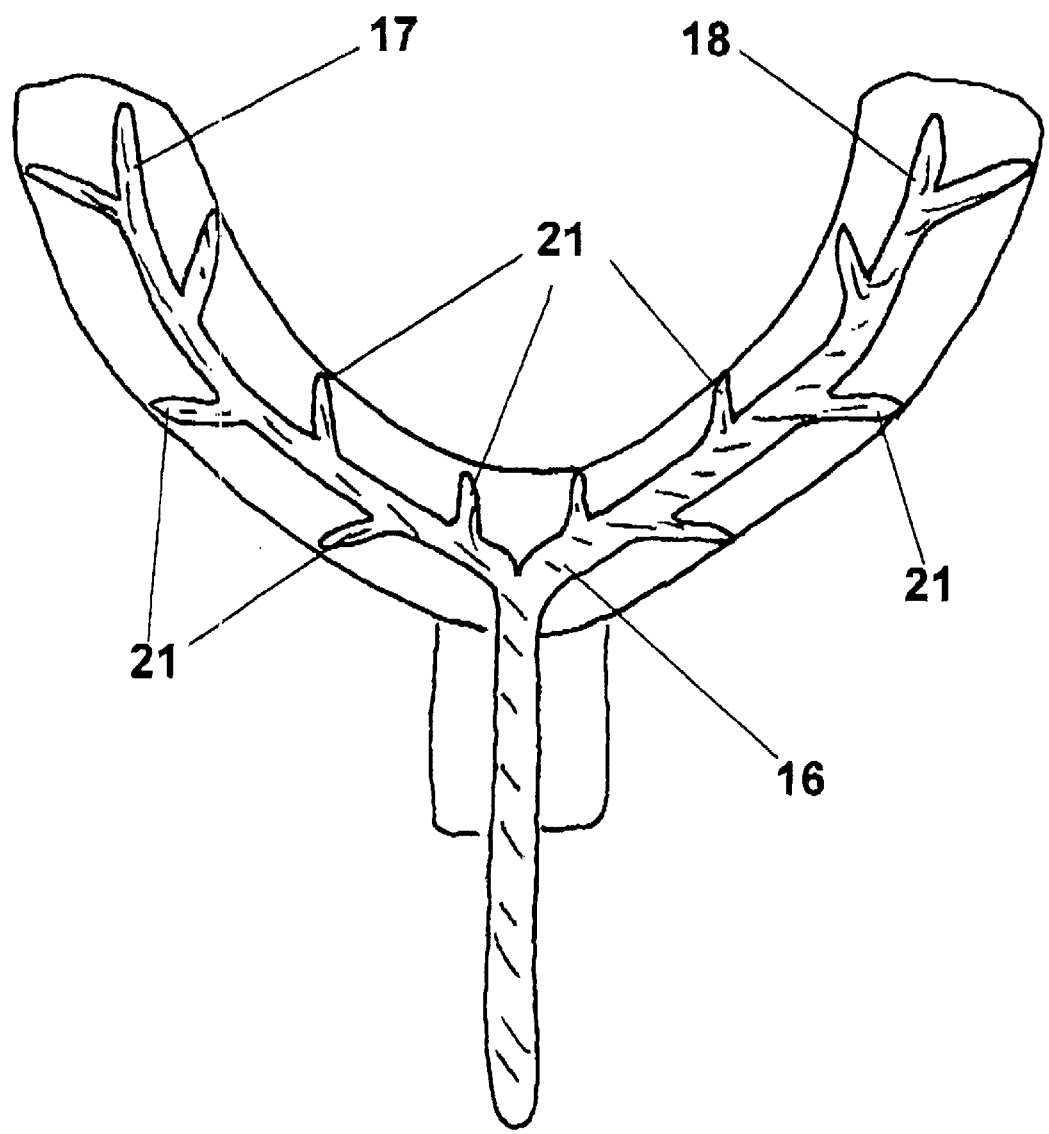
FIG. 10 a sectional view of a casting channel mold with tapering side struts.

In a further embodiment of the invention as depicted in FIGS. 4–7, a groove 11 is made in the bottom 2. Into this groove, a removable casting channel mold can be inserted, as is depicted in FIGS. 8–10.

The groove 11 has an essentially Y-shaped progression with two paired ends 12, 13 and a singular end 14. The singular end 14 corresponds to a hole 15 that is conically tapering in cross-section in a first approximation and is integrated into the handle 10 of the impression tray.

In an impression tray of this type, a casting channel mold, as is described further below, is placed in the groove 11 and then the U-shaped groove 1 is filled with hardening silicone and a first preliminary impression is taken of the patient's set of teeth. After the silicone hardens, the casting channel mold is pulled out of the casting material, such that above the groove 11, a hollow casting channel occurs in the hardened silicone.

Since the casting channel mold is connected to the hole 15 in the handle 10, an access to the casting channel is thus created via the hole 15 after removing the casting channel mold. By this hole, a lower-viscosity casting material can then be pressed into the casting channel.

In order to introduce this lower-viscosity casting material, a syringe can in the process be inserted into the hole 15. Since because of the essentially conical progression of the hole, this hole has a wide range of diameters, the projection existing on a syringe can also be very different. By the conical progression of the hole, an increased variability is thus achieved in regard to the syringes to be set on this hole.

It is assumed that when the patient bites down, he bites down on the casting channel, so that after removal of the casting channel mold, when the impression tray is re-inserted on the patient's jaw, lower-viscosity material can be injected via the casting channel, so that the tooth locations are cast even more precisely than the preliminary casting material.

Should during biting down in the preliminary impression material, no connections result as aforementioned between the casting channel and the hollow space caused by a tooth, they can be subsequently formed in the hardened preliminary impression material if necessary with a tool such as a scalpel or the like.

In FIG. 6 it is recognized that a casting channel mold 6 can have essentially a mushroom-shaped cross-section, so that the groove 11, in which the casting channel mold 16 is inserted, is covered by the casting channel mold 16. However, it is also possible that the cross-section of a casting channel mold 16, as recognized in FIG. 7, is essentially a rectangle. A shape of this type is easier to manufacture.

Figure 4:
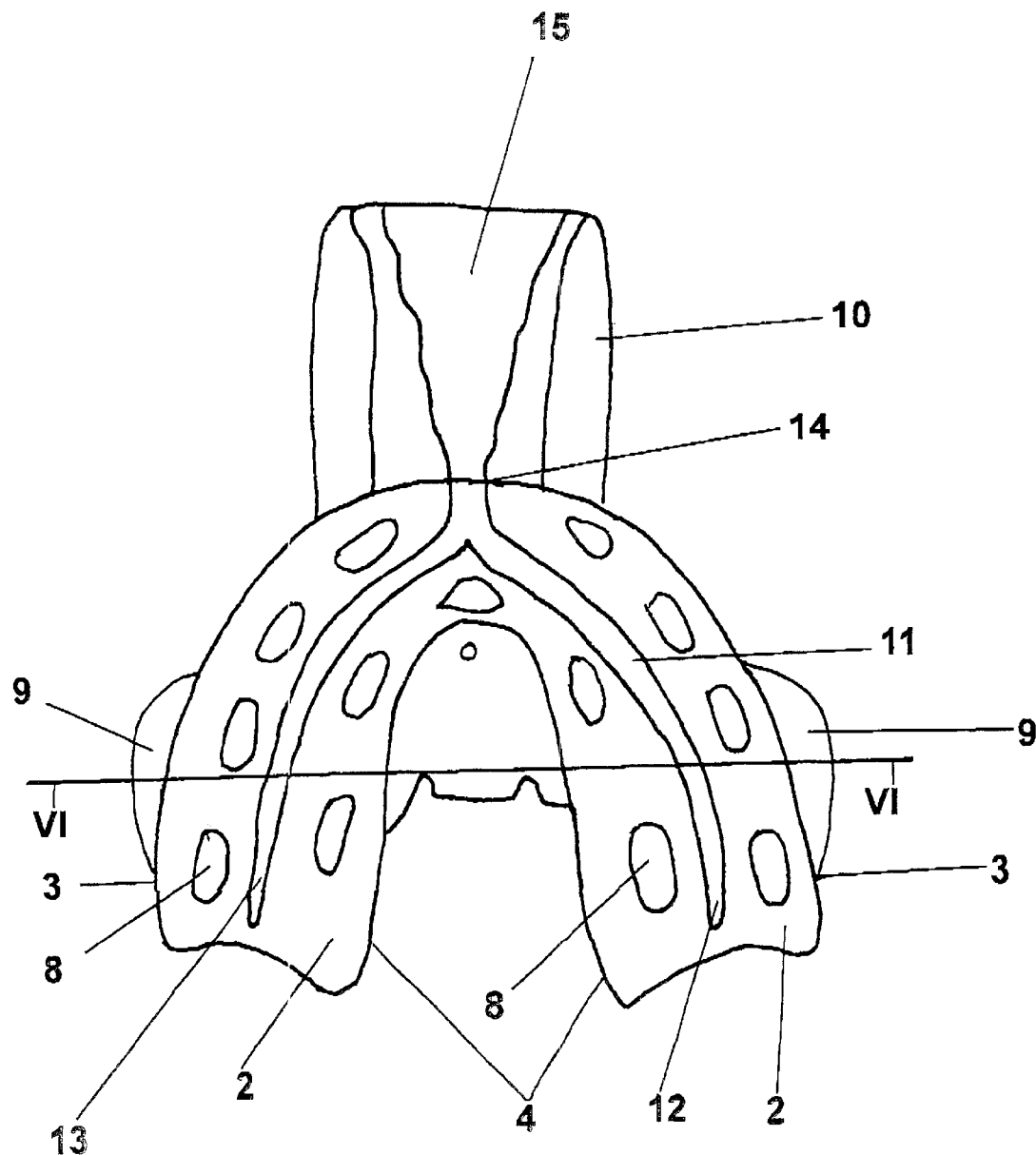
FIG. 4 a perspective view of an impression tray with a molded groove to receive a casting channel mold.
Figure 5:
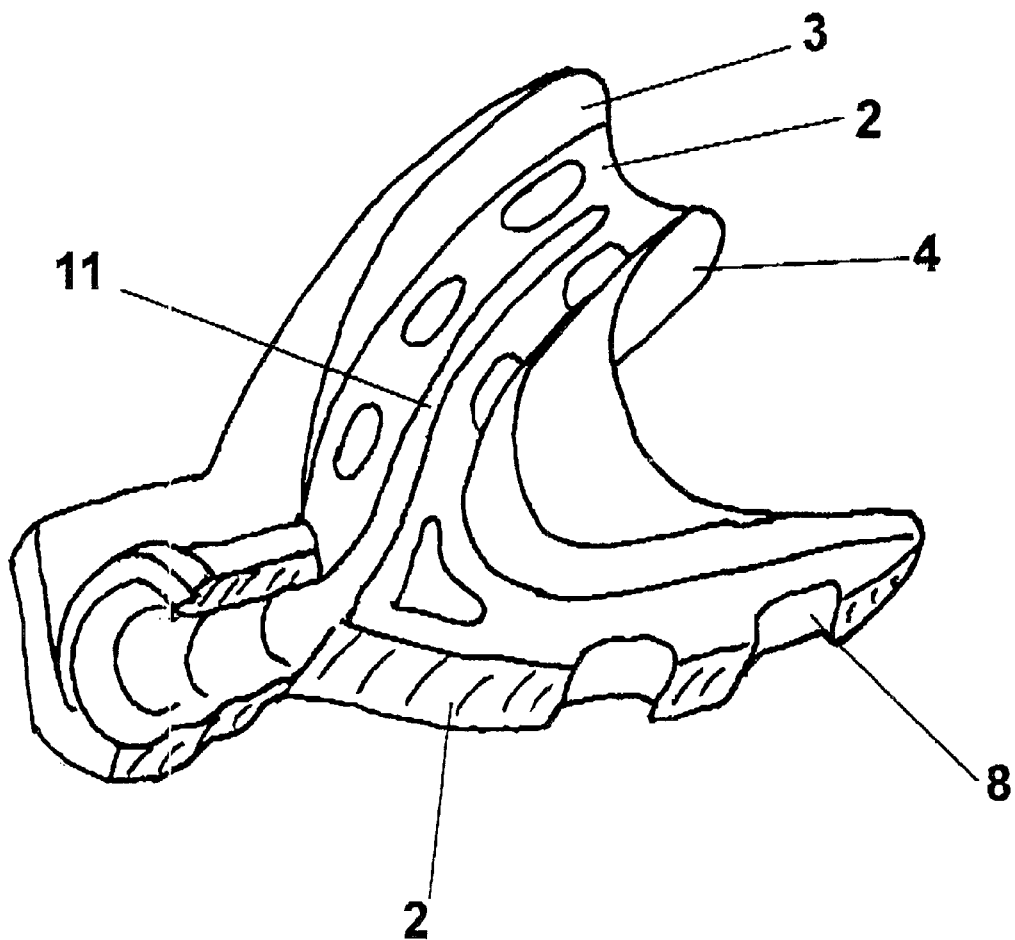
FIG. 5 a partially cut perspective view of an impression tray according to FIG. 4.

As is recognized in the view in FIG. 8, the casting channel mold is essentially constructed with a Y-shaped contour, whereby the two paired sections are constructed with a cross-section that tapers to its ends, as can be recognized in FIG. 9 in the side view. It can be recognized in this side view as well that on the underside of the casting channel mold 16, a projection 19 runs with which the casting channel mold 16 can be inserted in the groove 11 at the bottom 2 of an impression tray as shown in FIGS. 4 and 5.

Furthermore, it is additionally recognized in FIGS. 8 and 9, that the singular end 19 of the casting channel mold 16 is constructed with a handle loop 20. By this handle loop, the casting channel mold 16 can be pulled out of the casting channel if the preliminary impression material sitting over the casting channel mold has hardened so that the low-viscosity casting material can be injected as described above into the hollow space that results.

As mentioned and as can also be easily seen in FIG. 9, the casting channel mold has a cross-section that tapers to its paired ends. This not only has the advantage that the casting channel mold is easier to remove from the preliminary impression material by pulling on the grip loop, but also causes the casting channel mold to cause a thickening of the bottom when the bottom has a parallel upper side and lower side, through which as described above, a biting down can be achieved by the application of normal forces only, during the molding of a jaw impression.

Fundamentally, a casting channel mold of this type can also be inserted into an impression tray according to the state of the art without the presence of a corresponding groove 11 necessary for this.

A casting channel mold provided for this is depicted in FIG. 10. In this casting channel mold, side struts 21 tapering on the paired ends 17, 18 are molded on over their progression. These side struts function for the purpose of placing a casting channel mold into the U-shaped groove of an impression tray, depicted only in dots and dashes, without the special groove 11, whereby these side struts then affix the casting channel mold 16 or its paired ends 17, 18 in the right position.

The side struts 21 are in the process, on the one hand, in turn constructed so that they are slightly tapering so that they can be more easily removed. On the other hand, they are also somewhat sloping so as not to prevent the pulling out of the casting channel mold 16 out of the hardened preliminary casting material in a barblike manner.

With a casting channel mold of this type that is tapering towards its ends in cross-section, it can be achieved that also in the customary impression trays, a thickening occlusal overlay area is formed so that an impression tray can be held by a patient when he is biting, without tilting the impression tray.—Is prevented by the inserted casting channel mold.

What is claimed is:

1. An impression tray article for dental prosthetics comprising:

a mouthpiece having a central portion with legs extending therefrom, said mold having a U-shaped running groove extending along said legs and said central portion, said groove having a bottom and two side walls, said bottom having a thickness that increases from respective ends of said legs toward said central portion, said bottom having a groove means formed therein for receiving a removable casting channel mold therein.

2. The article of claim 1, said bottom having an upper side having a curve rising at the respective ends of said legs.

3. The article of claim 1, said bottom having an upper side with a lateral slope extending toward said central portion, said lateral slope corresponding to a Wilson's curve.

4. The article of claim 1, said two side walls extending along said legs and beyond said bottom at the respective ends of said legs, said side walls and said bottom at the respective ends of said legs defining a U-shaped counter-bite groove.

5. The article of claim 1, said bottom having a plurality of holes formed therethrough.

6. The article of claim 1, further comprising:

a handle molded to said central portion of said mouthpiece, said handle having a hole formed therein, said hole communicating with said groove, said hole suitable for receiving a projection piece of the casting channel mold therein.

7. The article of claim 6, said hole having a conical shape with a cross-section that narrows in diameter toward said groove.

8. An impression tray article for dental prosthetics comprising:

a mouthpiece having a central portion with legs extending therefrom, said mold having a U-shaped running groove extending along said legs and said central portion, said groove having a bottom and two side walls; and a casting channel mold removably received in said groove, said casting channel mold having a U-shaped contour, said casting channel mold having a cross-section tapering toward the respective ends of said legs.

9. The article of claim 8, said casting channel mold having a Y-shape, one end of said casting channel mold having a grip loop formed therein.

10. The article of claim 8, said casting channel mold having tapering side struts extending outwardly therefrom.

* * * * *